(12) United States Patent
Sano et al.

(10) Patent No.: US 10,533,849 B2
(45) Date of Patent: Jan. 14, 2020

(54) ANALYSIS APPARATUS AND ANALYSIS PROGRAM

(71) Applicant: TOYOTA JIDOSHA KABUSHIKI KAISHA, Toyota-shi, Aichi-ken (JP)

(72) Inventors: Yohei Sano, Toyota (JP); Yuichi Hirano, Nisshin (JP)

(73) Assignee: TOYOTA JIDOSHA KABUSHIKI KAISHA, Toyota-shi, Aichi-ken (JP)

(*) Notice: Subject to any disclaimer, the term of this patent is extended or adjusted under 35 U.S.C. 154(b) by 0 days.

(21) Appl. No.: 16/375,194

(22) Filed: Apr. 4, 2019

(65) Prior Publication Data

US 2019/0331483 A1    Oct. 31, 2019

(30) Foreign Application Priority Data

Apr. 27, 2018    (JP) .................................. 2018-087114

(51) Int. Cl.
| | | |
|---|---|---|
| *G01B 11/30* | (2006.01) | |
| *G01N 21/94* | (2006.01) | |
| *B05C 11/10* | (2006.01) | |
| *G06N 3/08* | (2006.01) | |

(52) U.S. Cl.
CPC .......... *G01B 11/30* (2013.01); *B05C 11/1005* (2013.01); *G01N 21/94* (2013.01); *G06N 3/08* (2013.01)

(58) Field of Classification Search
CPC .... G01N 21/9054; G01N 21/94; B06C 21/00; G01B 11/30; G06N 3/08; G05C 11/1005
USPC ........................................................ 356/237.3
See application file for complete search history.

(56) References Cited

U.S. PATENT DOCUMENTS

| | | | |
|---|---|---|---|
| 2015/0035970 A1* | 2/2015 | Brumbaugh | ....... G01N 21/9054 348/93 |
| 2019/0011252 A1* | 1/2019 | Moeller | .................. B05C 21/00 |

FOREIGN PATENT DOCUMENTS

| | | |
|---|---|---|
| JP | 2005-118757 A | 5/2005 |
| JP | 2013-113657 A | 6/2013 |

* cited by examiner

*Primary Examiner* — Hung Nguyen
(74) *Attorney, Agent, or Firm* — Sughrue Mion, PLLC

(57) ABSTRACT

An analysis apparatus includes: a storage unit configured to store a learned neural network; an acquisition unit configured to acquire determination image data obtained by capturing an image of a surface in which at least a surface layer of a coating layer stacked on the coating irregularity generated in the coating surface to be determined has been abraded; a determination unit configured to input the determination image data acquired by the acquisition unit to the learned neural network read out from the storage unit and determine the cause of occurrence of the coating irregularity generated in the coating surface to be determined; and an output unit configured to output information regarding the cause of occurrence determined by the determination unit.

7 Claims, 8 Drawing Sheets

| LEARNING IMAGE DATA | INPUT DATA (CAUSE OF OCCURRENCE) |
|---|---|
|  | IRON IRREGULARITY |
|  | COATING AGENT |
|  | MIDDLE PH RESIDUE |
|  | ELECTRODEPOSITION RESIDUE |
|  | ATTACHMENT OF VINYL CHLORIDE |
|  | ELECTRODEPOSITION GAS |
|  | STAIN |
|  | GRINDING RESIDUE |
| ⋮ | ⋮ |

| LEARNING IMAGE DATA BEFORE ABRASION | LEARNING IMAGE DATA | INPUT DATA (CAUSE OF OCCURRENCE) |
|---|---|---|
|  |  | IRON IRREGULARITY |
|  |  | COATING AGENT |
|  |  | MIDDLE PH RESIDUE |
|  |  | ELECTRODEPOSITION RESIDUE |
|  |  | ATTACHMENT OF VINYL CHLORIDE |
|  |  | ELECTRODEPOSITION GAS |
|  |  | STAIN |
|  |  | GRINDING RESIDUE |
| ⋮ | ⋮ | ⋮ |

ANALYSIS APPARATUS AND ANALYSIS PROGRAM

CROSS REFERENCE TO RELATED APPLICATIONS

This application is based upon and claims the benefit of priority from Japanese patent application No. 2018-87114, filed on Apr. 27, 2018, the disclosure of which is incorporated herein in its entirety by reference.

BACKGROUND

The present disclosure relates to an analysis apparatus and an analysis program.

An apparatus configured to determine, when a coating defect has occurred, a cause of this coating defect based on coating defect data and coating condition data that have been input thereto has been known (see, for example, Japanese Unexamined Patent Application Publication No. 2005-118757).

SUMMARY

According to related art, since it is required to input the coating defect data and the coating condition data, the state of the coating defect needs to be analyzed first, which analysis is troublesome and takes time before the cause of the coating defect is found.

The present disclosure provides an analysis apparatus and the like capable of analyzing a cause of occurrence of a coating irregularity, which is a coating defect that appears on a coating surface as a protrusion, easily and with a high degree of accuracy in a short period of time.

An analysis apparatus according to a first aspect of the present disclosure is an analysis apparatus configured to analyze a cause of occurrence of a coating irregularity, which is a coating defect that appears on a coating surface as a protrusion, the analysis apparatus including: a storage unit configured to store a learned neural network that has performed learning using a combination of learning image data obtained by capturing an image of a surface in which at least a surface layer of a coating layer stacked on the coating irregularity generated in the coating surface to be learned has been abraded and input data estimated by analyzing this coating irregularity as training data; an acquisition unit configured to acquire determination image data obtained by capturing an image of a surface in which at least a surface layer of a coating layer stacked on the coating irregularity generated in the coating surface to be determined has been abraded; a determination unit configured to input the determination image data acquired by the acquisition unit to the learned neural network read out from the storage unit and determine the cause of occurrence of the coating irregularity generated in the coating surface to be determined; and an output unit configured to output information regarding the cause of occurrence determined by the determination unit. In this way, the image data obtained from a simple work of abrading at least the surface layer of the coating layer of the coating defect is used as target image data handled in the neural network, whereby it is possible to provide an analysis apparatus capable of analyzing the cause of occurrence of the coating irregularity easily and with a high degree of accuracy in a short period of time.

In the aforementioned analysis apparatus, when the coating irregularity occurs due to dust, each of the learning image data and the determination image data may be image data obtained by capturing an image of the surface abraded in such a way that the dust is exposed. By preparing the image data obtained by capturing the image of the surface which is in the state in which dust is exposed, accuracy of determination is improved. Further, when the determination unit cannot make a determination that satisfies a predetermined determination criterion, the determination unit may make a determination that determination image data obtained by capturing an image of a surface in which the coating layer to be determined is further abraded is required. By requiring the image data in which the abrading amount has been changed, it is possible to achieve determination with a higher accuracy.

Further, in the aforementioned analysis apparatus, the storage unit may store a plurality of learned neural networks for respective coating colors, and the determination unit may select the learned neural network that receives the determination image data based on a coating color indicated by the determination image data acquired by the acquisition unit. By constructing the learned neural networks for the respective coating color and selectively using one of them, accuracy of determination can be further improved.

Further, in the aforementioned analysis apparatus, the training data may include learning image data before abrasion obtained by capturing an image of a surface before the coating layer is abraded, the acquisition unit may acquire determination image data before the abrasion obtained by capturing an image of a surface in which the coating layer to be determined has not been abraded, and the determination unit may input the determination image data before the abrasion acquired by the acquisition unit to the learned neural network read out from the storage unit and determine the cause of occurrence of the coating irregularity generated in the coating surface to be determined. According to the aforementioned configuration, it is possible to easily obtain the result of the determination even when the coating surface to be determined is not abraded. Therefore, it is possible to reduce time and trouble of the work.

In this case, the acquisition unit may acquire the determination image data when the determination unit has not determined the cause of occurrence, and the determination unit may input the determination image data after the abrasion acquired by the acquisition unit to the learned neural network, and determine the cause of occurrence of the coating irregularity generated in the coating surface to be determined. While it is expected that the accuracy of determination may decrease when the coating surface is not abraded, when a certain accuracy cannot be secured, re-determination may be performed by using the determination image data after the abrasion, whereby it is possible to achieve both the accuracy of determination and a simple determination.

An analysis program according to a second aspect of the present disclosure is an analysis program configured to analyze a cause of occurrence of a coating irregularity, which is a coating defect that appears on a coating surface as a protrusion, the analysis program causing a computer to execute the following steps of: an acquisition step for acquiring determination image data obtained by capturing an image of a surface in which at least a surface layer of a coating layer stacked on the coating irregularity generated in the coating surface to be determined has been abraded; a reading step for reading out a learned neural network that has performed learning using a combination of learning image data obtained by capturing an image of a surface in which at least a surface layer of a coating layer stacked on the coating irregularity generated in the coating surface to be learned has been abraded and input data estimated by analyzing this coating irregularity as training data from a storage unit; a determination step for inputting the determination image data acquired in the acquisition step to the learned neural network read out from the storage unit and determining the cause of occurrence of the coating irregularity generated in the coating surface to be determined; and an output step for outputting information regarding the cause of occurrence determined in the determination step. In this way, the image data obtained from a simple work of abrading at least the surface layer of the coating layer of the coating defect is used as target image data handled in the neural network, whereby it is possible to provide an analysis program capable of analyzing the cause of occurrence of the coating irregularity easily and with a high degree of accuracy in a short period of time.

According to the present disclosure, it is possible to analyze a cause of occurrence of a coating irregularity, which is a coating defect that appears on a coating surface as a protrusion, easily and with a high degree of accuracy in a short period of time.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Figure 1:
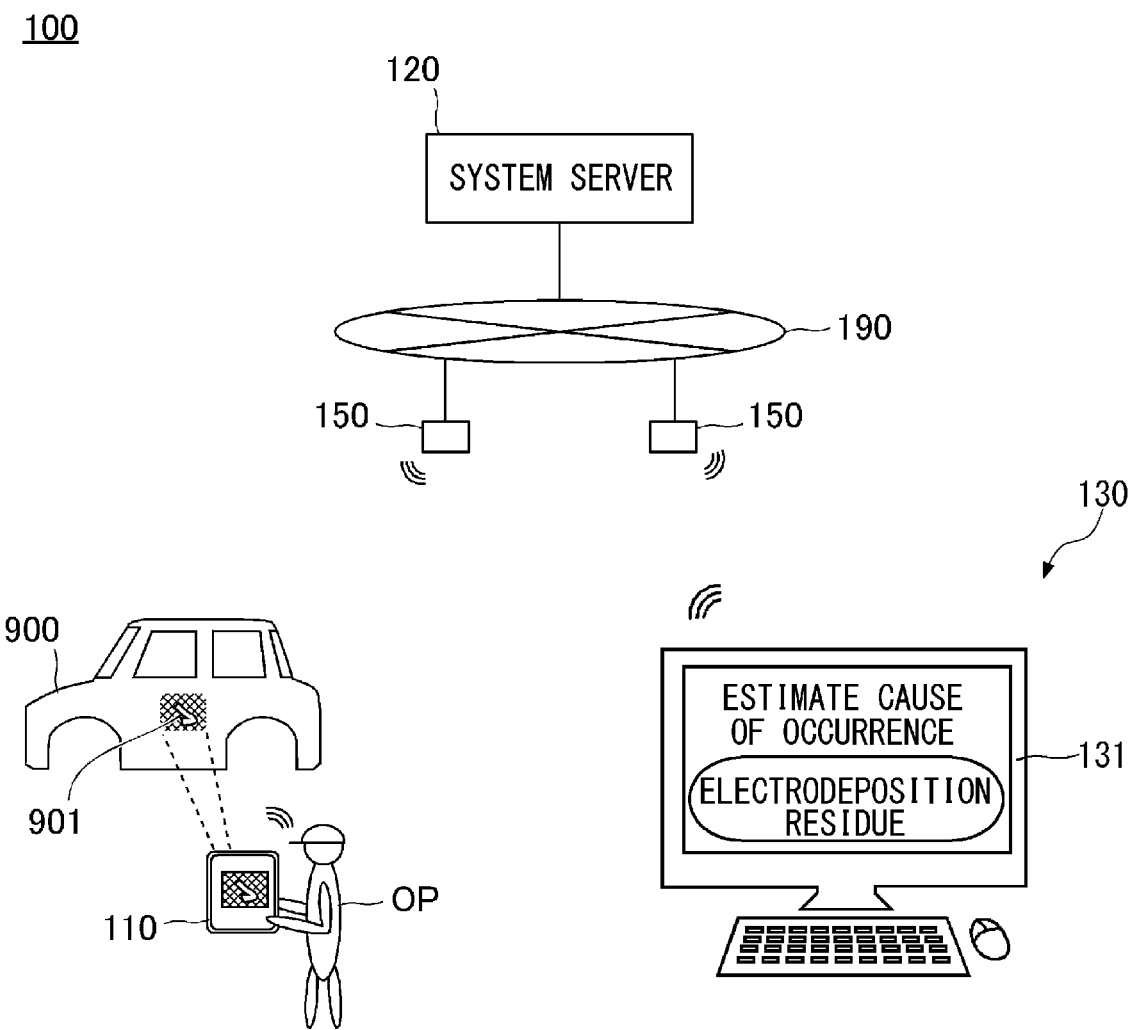
FIG. 1 is an overall conceptual diagram showing an overall configuration of an analysis system.

FIG. 1 is an overall conceptual diagram showing an overall configuration of an analysis system 100. The analysis system 100 is, for example, an analysis system configured to analyze a cause of occurrence of a coating irregularity found on a coating surface of a vehicle body 900 of an automobile. The coating irregularity, which is a coating defect that appears on the coating surface as a protrusion, is generated due to dust attached to the coating surface during coating or air bubbles mixed into paint. The analysis system 100 determines the cause of the coating irregularity that has been found using a neural network.

When an operator OP observes the vehicle body 900 that has been subjected to a coating process or the vehicle body 900 during the coating process and finds a coating irregularity 901, the operator OP slightly abrades the surface thereof and captures an image of this coating irregularity by a camera of an input terminal 110. The operator OP operates the input terminal 110 and transmits the image data of the image that has been captured to a system server 120 via wireless communication.

The system server 120, which is connected to the Internet 190, acquires this image data via a wireless router 150. The system server 120 determines the cause of occurrence of the coating irregularity in the image using a learned neural network as an analysis apparatus that analyzes the cause of occurrence of a coating irregularity. Then the system server 120 outputs the information regarding the cause of occurrence that has been determined to an output terminal 130 via the Internet 190 and the wireless router 150.

The output terminal 130 displays the information regarding the cause of occurrence received from the system server 120 to a display monitor 131. A coating manager is able to recognize the cause of occurrence determined in the system server 120 through the display monitor 131.

Note that the configuration of the analysis system 100 that includes the system server 120 as a main component may be configured in various ways. The information regarding the cause of occurrence may be displayed on a display screen of the input terminal 110, or the system server 120 and the output terminal 130 may be connected to each other by wired communication. Further, the Internet 190 may not be used and a limited network may instead be used in such a way that the analysis system 100 is disconnected from the external network. Further, an image of the coating irregularity 901 may be captured by constructing an automatic photographing system instead of capturing an image of the coating irregularity 901 by the operator OP operating the input terminal 110. The process of abrading the surface layer may be automated. Further, an image server that accumulates the image data may be separately provided.

Figure 2:
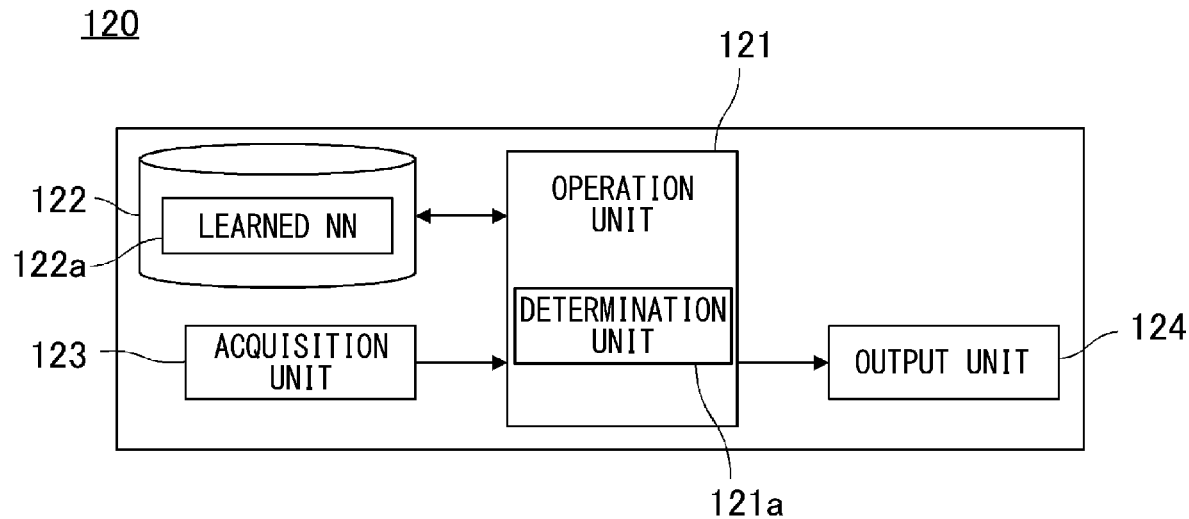
FIG. 2 is a block diagram showing a configuration of a system server.

The system server 120 will now be explained. FIG. 2 is a block diagram showing a configuration of the system server 120. The system server 120 is mainly composed of an operation unit 121, a storage unit 122, an acquisition unit 123, and an output unit 124.

The operation unit 121 is, for example, a CPU, and performs the overall control of the system server 120 and various operation processing. The storage unit 122, which is, for example, a hard disc drive, stores, besides a software program executed by the operation unit 121, a learned neural network 122a (hereinafter this network will be referred to as a "learned NN 122a" or the like).

The acquisition unit 123 includes a communication interface to be connected to the Internet 190. The communication interface is, for example, a wireless LAN unit. The acquisition unit 123 acquires determination image data obtained by capturing an image of a coating irregularity, which is a determination target, and transfers the determination image data to the operation unit 121.

Upon receiving the determination image data from the acquisition unit 123, the operation unit 121 reads out the leaned NN 122a from the storage unit 122. The determination unit 121a, which is a function execution unit served by the operation unit 121, inputs the determination image data into the learned NN 122a, determines the cause of occurrence of the coating irregularity generated in the coating surface to be determined, and transfers the result of the determination to the output unit 124.

The output unit 124 includes a communication interface to be connected to the Internet 190. Alternatively, the output unit 124 may use the communication interface of the acquisition unit 123. The output unit 124 outputs the information regarding the cause of occurrence determined by the determination unit 121a to the output terminal 130.

Figure 3:
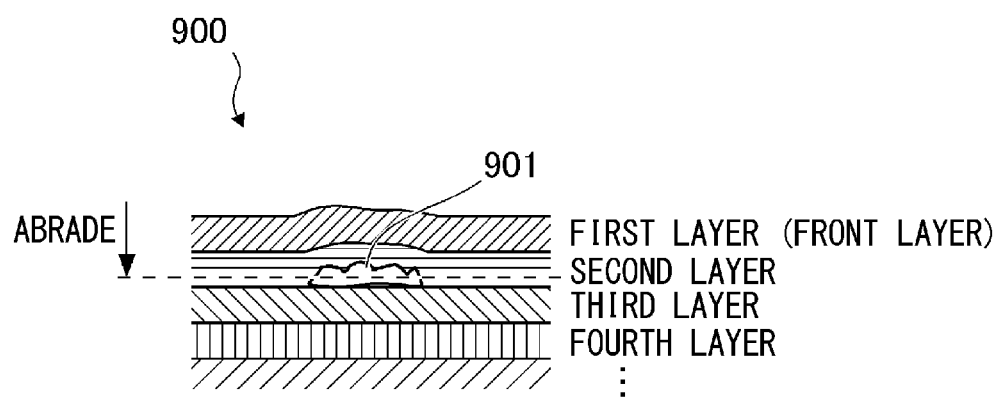
FIG. 3 is an enlarged cross-sectional view of a part in the vicinity of a surface where a coating irregularity has occurred.

FIG. 3 is an enlarged cross-sectional view of a part in the vicinity of the surface where the coating irregularity 901 has occurred. The coating of the vehicle body 900 in several layers is performed on a base in an overlapping manner. As shown in FIG. 3, when a surface layer facing the outer environment is denoted by a first layer, a second layer is closer to the base than the first layer is, which means that the second layer is formed in a coating process earlier than the coating process where the first layer is formed, and a third layer is closer to the base than the second layer is, which means that the third layer is formed in a coating process earlier than the coating process where the second layer is formed. When, for example, dust is attached during the coating process of the second layer and the coating irregularity 901 is generated, the coating surfaces of the second layer and the first layer bulge, which results in a painting defect.

The learned NN 122a according to this embodiment is a neural network that has performed learning using a combination of learning image data obtained by capturing an image of the surface in which at least a surface layer of the coating layer stacked on the coating irregularity generated in the coating surface has been abraded and the input data estimated by analyzing this coating irregularity as training data. When the coating irregularity is due to dust, as shown in FIG. 3, the learning image data may be a captured image of the surface abraded to a depth indicated by the dashed line in such a way that the dust is exposed. While features of the coating irregularity can be taken as an image relatively easily by simply abrading the surface layer, it is possible to cause the neural network to perform learning more efficiently by using an image in the state in which the dust is exposed, which enables accuracy of determination of the cause of occurrence of the coating irregularity to be improved.

Figure 4:
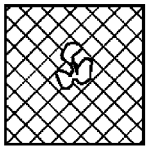
FIG. 4 is a diagram for illustrating training data.
Figure 4:
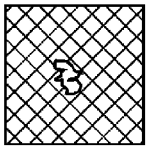
Figure 4:
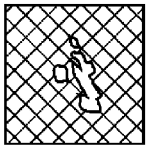
Figure 4:
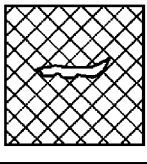
Figure 4:
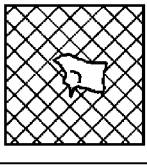
Figure 4:
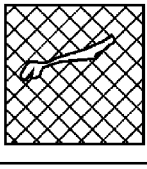
Figure 4:
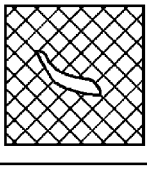
Figure 4:
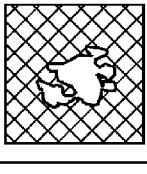

FIG. 4 is a diagram illustrating the training data. In a learning stage of the neural network, first, an expert inputs, for example, causes of occurrence of the coating irregularity estimated based on his/her knowledge and experience into a terminal while checking the images of the respective pieces of learning image data. The input data that has thus been input is combined with this learning image data, which forms the training data. Then the neural network is caused to perform supervised learning using the learning image data as input information and using the combined input data as a correct answer of output.

As shown in FIG. 4, there are various shapes, ways of exposure and the like of the learning images obtained by capturing an image of the surface in which at least a surface layer has been abraded. An expert associates the estimated causes of occurrence such as, for example, "iron irregularity", "coating agent", "middle PH residue" or the like with the respective images. By preparing a certain pieces of training data that has thus been formed and causing the neural network to learn these data items, the learned NN 122a is generated. The learned NN 122a that has been generated is transferred to the storage unit 122 of the system server 120 and is put to practical use. The cause of occurrence may be specified based on scientific analysis without relying on expert knowledge and experience, and may be associated with the learning image data.

Figure 5:
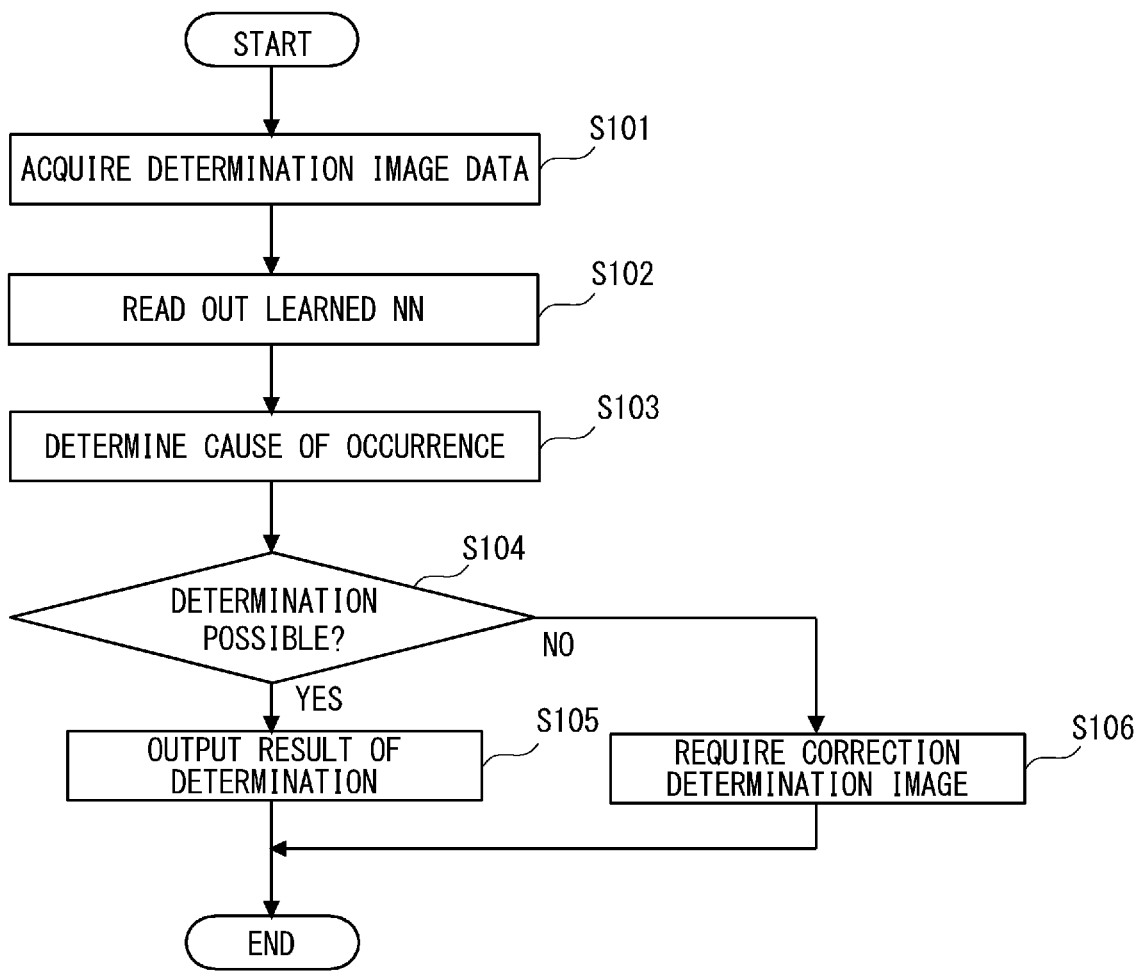
FIG. 5 is a flowchart showing a process flow of a system server.

Next, processing executed by the system server 120 will be explained. FIG. 5 is a flowchart showing a process flow of the system server 120.

In Step S101, the acquisition unit 123 acquires the determination image data obtained by capturing the image of the coating surface to be determined. The determination image data is, similar to the aforementioned learning image data, image data obtained by capturing an image of the surface in which at least a surface layer on the coating irregularity has been abraded. The acquisition unit 123 transfers the determination image data that has been acquired to the determination unit 121a.

In Step S102, the determination unit 121a reads out the learned NN 122a from the storage unit 122. Then, in Step S103, the determination image data that has been acquired is input to the learned NN 122a that has been read out, thereby determining the cause of occurrence of the coating irregularity.

The determination unit 121a checks whether the cause of occurrence of the coating irregularity has been determined in Step S104. The determination unit checks whether the cause of occurrence of the coating irregularity has been determined depending on whether a determination that satisfies a predetermined determination criterion has been made. When, for example, none of the categories (causes of occurrence) prepared as the output of the learned NN 122a has exceeded the probability (e.g., 75%), which is a predetermined threshold, it is determined that the cause of occurrence has not been determined.

When it is determined in Step S104 that the cause of occurrence of the coating irregularity has been determined, the process goes to Step S105, where the determination unit 121a transfers the cause of occurrence that has been determined to the output unit 124, and the output unit 124 outputs this information to the output terminal 130. When, for example, the output unit 124 cannot output this information to the output terminal 130 due to the reason that the communication has not been established or the like, the output unit 124 may store this information in the storage unit 122.

When it is determined in Step S104 that the cause of occurrence of the coating irregularity has not been determined, the process goes to Step S106, where the determination unit 121a determines that determination image data obtained by capturing an image of the surface in which the coating layer to be determined is further abraded is required and transfers this information to the output unit 124. The output unit 124 outputs this information to the output terminal 130. When the processing of Step S105 or S106 is completed, a series of processing is ended.

As described above, the coating manager is able to recognize the cause of occurrence of the coating irregularity by simply sending the image data obtained by a simple work of abrading the surface of the coating defect to the system server 120. By preparing a certain number of pieces of training data and increasing the accuracy of determination of the learned NN 122a, it is possible to obtain an analysis apparatus capable of analyzing the cause of occurrence of the coating irregularity easily and with a high degree of accuracy in a short period of time. Accordingly, it becomes possible to review the coating process in a short period of time and to improve yield in the coating process.

Figure 6:
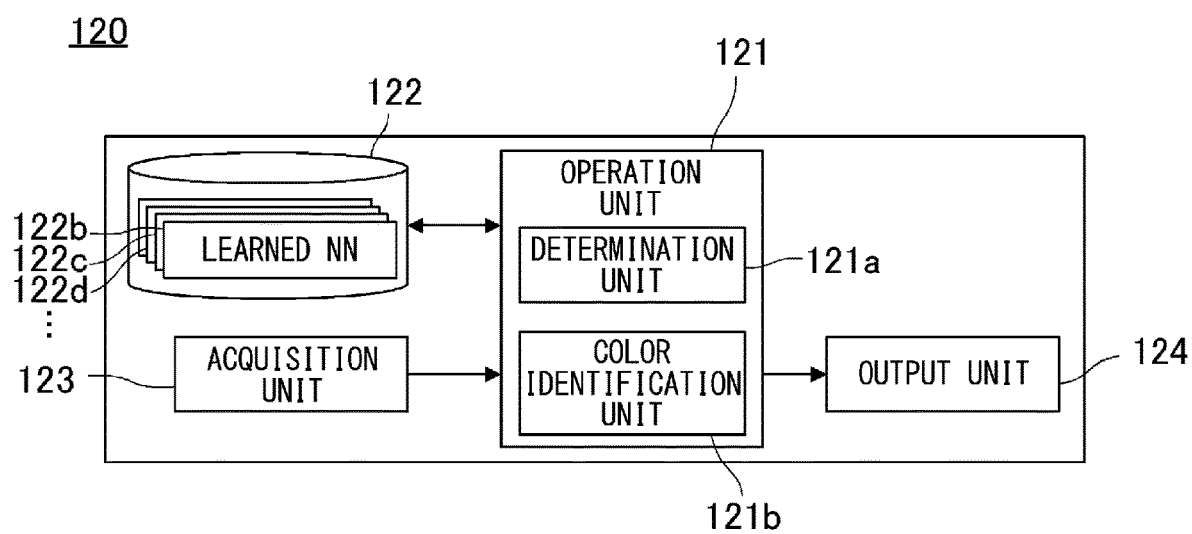
FIG. 6 is a block diagram showing a configuration of a system server according to a first modified example.

Next, some modified examples will be explained. FIG. 6 is a block diagram showing a configuration of a system server according to a first modified example. The system server 120 according to the first modified example is different from the system server 120 shown in FIG. 2 in that the operation unit 121 includes a color identification unit 121b as a function execution unit and the storage unit 122 stores plurality of learned NNs 122b, 122c, 122d . . . .

In this modified example, the learned neural network is prepared for each coating color of the surface layer. The learned NN 122b is, for example, a learned neural network that has performed learning using training data by learning image data obtained by capturing an image of a coating irregularity including a coating surface whose surface layer is red, and the learned NN 122c is a learned neural network that has performed learning using training data by learning image data obtained by capturing an image of a coating irregularity including a coating surface whose surface layer is blue.

The color identification unit 121b analyzes the determination image data and identifies the coating color of the surface layer to be determined. The color identification unit 121b extracts, for example, a peripheral image area that has not been abraded and performs color identification. The coating color that has been identified is transferred to the determination unit 121a.

The determination unit 121a reads out the learned NN that corresponds to the coating color identified by the color identification unit 121b from among the plurality of learned NNs 122b, 122c, 122d . . . stored in the storage unit 122, and determines, using the aforementioned learned NN, the cause of occurrence of the coating irregularity that has been generated in the coating surface to be determined.

Figure 7:
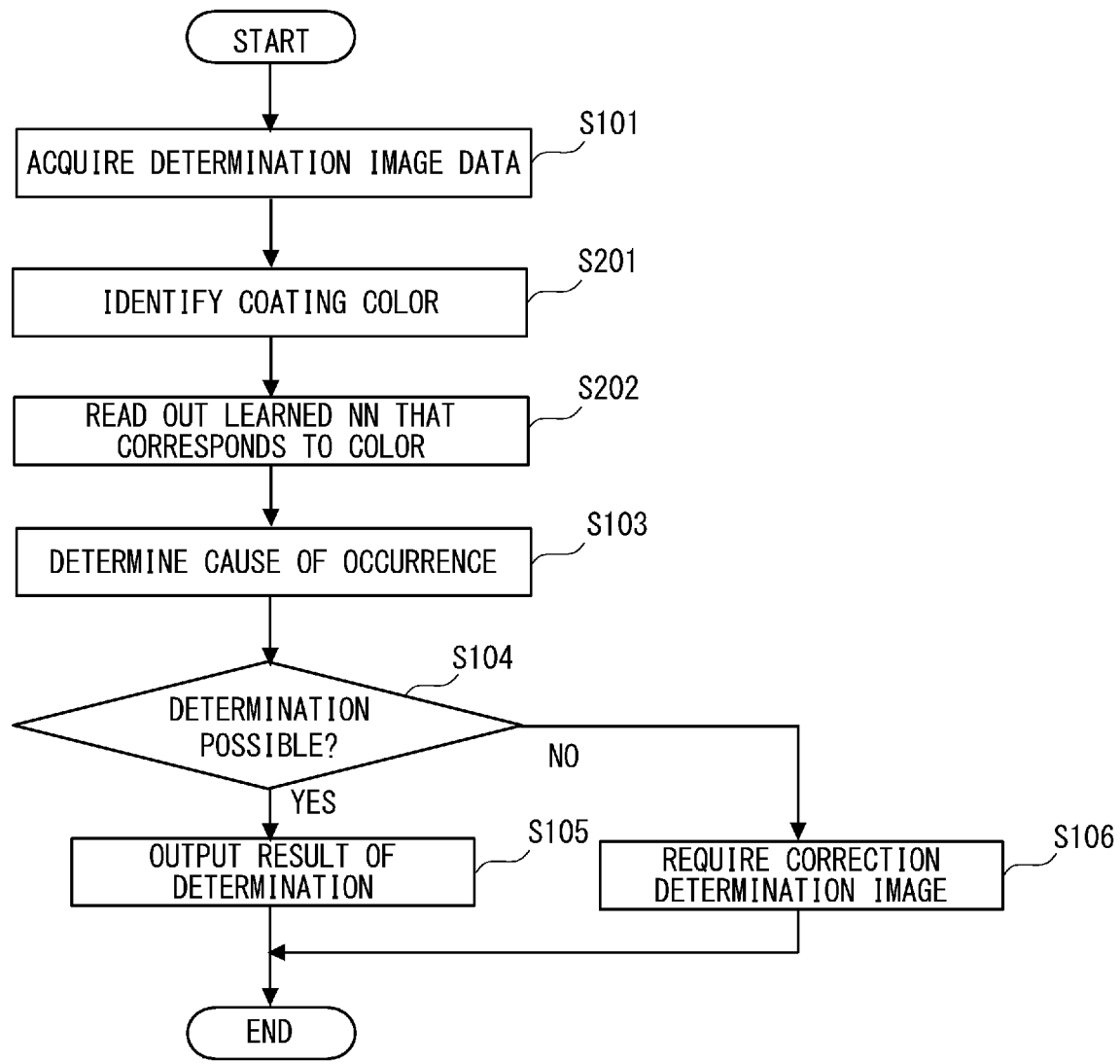
FIG. 7 is a flowchart showing a process flow of the system server according to the first modified example.

FIG. 7 is a flowchart showing a process flow of the system server 120 according to the first modified example. The flow that executes processing substantially the same as that in the flow shown in FIG. 5 is denoted by the reference symbols the same as those in FIG. 5, and descriptions thereof will be omitted unless otherwise specified.

When the acquisition unit 123 transfers the determination image data to the color identification unit 121b in Step S101, the process then goes to Step S201, where the color identification unit 121b identifies the coating color of the surface layer to be determined, as described above, and transfers the result of the identification to the determination unit 121a. Then the process goes to Step S202, where the determination unit 121a reads out, as described above, the learned NN that corresponds to the coating color identified by the color identification unit 121b from among the plurality of learned NNs 122b, 122c, 122d . . . stored in the storage unit 122. Then the process goes to Step S103, where the determination unit 121a determines the cause of occurrence of the coating irregularity generated in the coating surface to be determined using the specific learned NN read out in Step S202. By constructing the learned neural networks for the respective coating colors and selectively using one of them as in this modified example, it is possible to determine the cause of occurrence of the coating irregularity further accurately.

Figure 8:
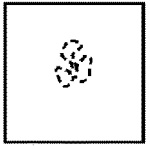
FIG. 8 is a diagram for illustrating training data according to a second modified example.
Figure 8:
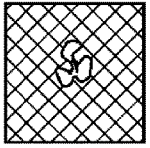
Figure 8:
Figure 8:
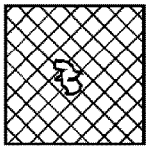
Figure 8:
Figure 8:
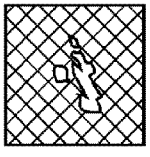
Figure 8:
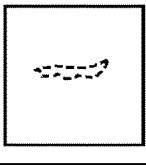
Figure 8:
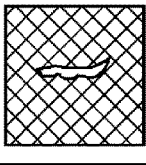
Figure 8:
Figure 8:
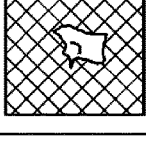
Figure 8:
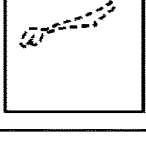
Figure 8:
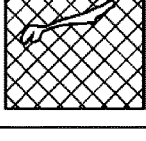
Figure 8:
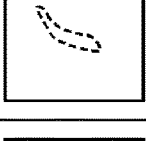
Figure 8:
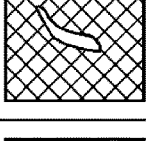
Figure 8:
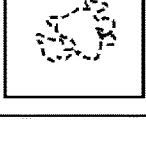
Figure 8:
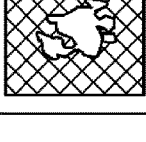

Next, a second modified example will be explained. FIG. 8 is a diagram illustrating training data according to the second modified example. The learned NN according to the second modified example is different from the learned NN generated by the training data described with reference to FIG. 4 in that the learned NN according to the second modified example also learns learning image data before abrasion in which the image of the surface before the coating layer is abraded is captured.

In the learning stage of the neural network according to the second modified example, first, for example, an expert inputs causes of occurrence of the coating irregularity estimated based on his/her knowledge and experience into a terminal while checking the images of the learning image data before the abrasion, the images of the learning image data, or both of these images. The input data that has thus been input is combined with the learning image data before the abrasion and the learning image data, thereby forming training data. Then, in the first stage, the neural network is caused to perform supervised learning using the learning image data before the abrasion as input information and using the combined input data as a correct answer of output. Next, in the second stage, the neural network is caused to perform supervised learning using the learning image data as the input information and using the combined input data as a correct answer of output. The cause of occurrence may be specified based on scientific analysis without relying on expert knowledge and experience, and this cause of occurrence may be associated with the learning image data before the abrasion and the learning image data.

The learned NN that has been generated is transferred to the storage unit 122 of the system server 120 and is put into practical use. The learned NN that has thus been generated includes two determination steps. That is, when the determination image data before the abrasion has been accepted as the input image data and a probable cause of occurrence has been determined, the result of this determination is output. When the probable cause of occurrence has not been determined, the determination image data after the abrasion is accepted as the input image data and a determination with a higher accuracy is performed.

By constructing the learned NN in the aforementioned way, it is possible to obtain the result of the determination in an easy way even when the coating surface to be determined is not abraded. Therefore, it is sufficient for the operator OP to first prepare the determination image data before the abrasion, which is data before the coating surface is abraded, whereby it is possible to reduce time and trouble of the work of abrading the coating surface. Further, when it is impossible to secure a certain accuracy in a simple determination, the operator OP prepares the determination image data after the coating surface is abraded, and the learned NN receives the determination image data after the abrasion and makes re-determination. By performing this re-determination, accuracy of determination can also be secured. That is, by using this learned NN, it becomes possible to ensure both work efficiency and accuracy of determination.

Figure 9:
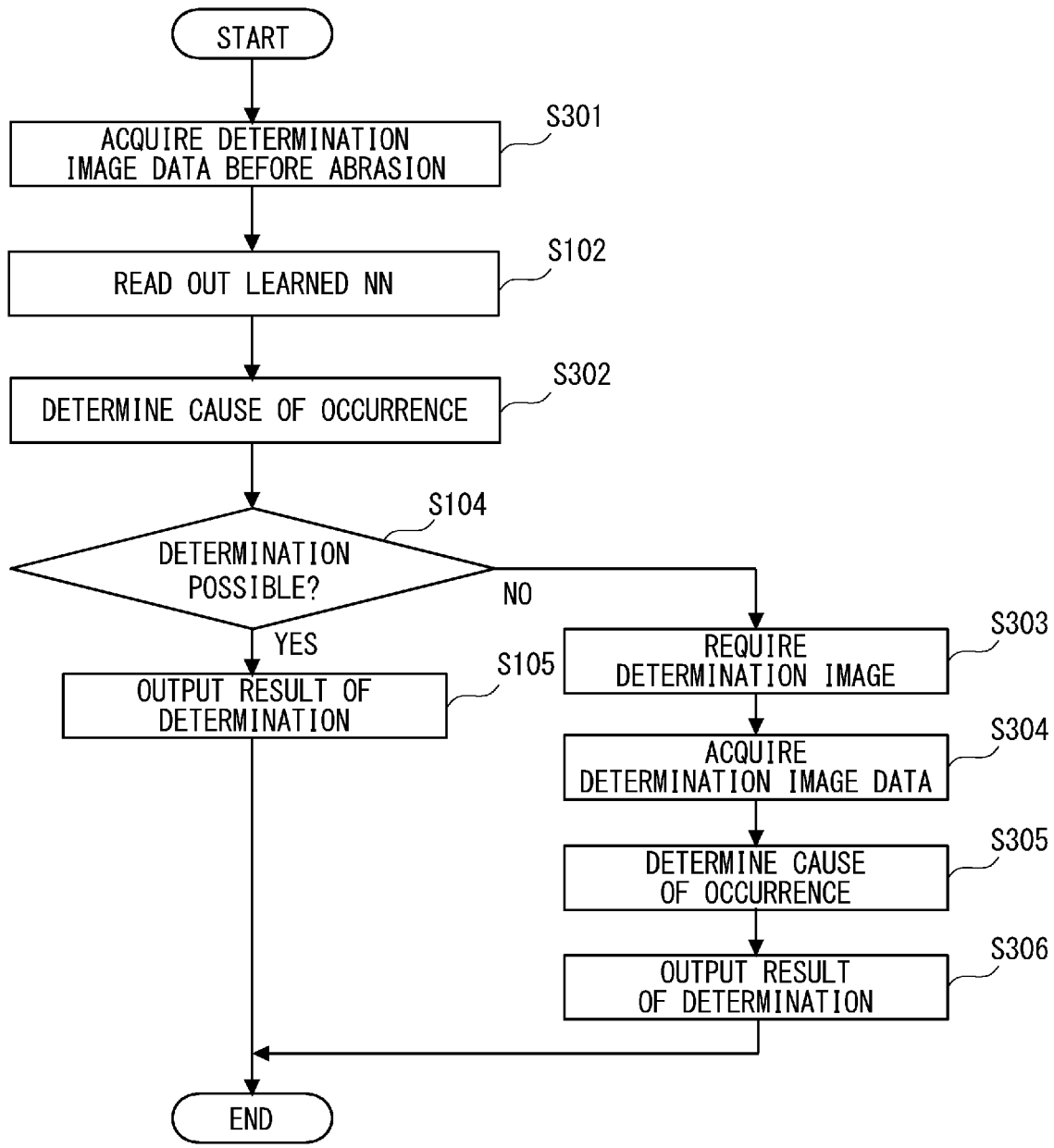
FIG. 9 is a flowchart showing a process flow of a system server according to the second modified example.

FIG. 9 is a flowchart showing a process flow of the system server 120 according to the second modified example. The flow that executes processing substantially the same as that in the flow shown in FIG. 5 is denoted by the reference symbols the same as those in FIG. 5, and descriptions thereof will be omitted unless otherwise specified.

In Step S301, the acquisition unit 123 acquires the determination image data before the abrasion in which an image of the coating surface to be determined is captured. The determination image data before the abrasion is image data obtained by capturing an image of a surface before the work of abrading the surface layer on the coating irregularity is performed. The acquisition unit 123 transfers the determination image data that has been acquired to the determination unit 121a.

After Step S102, in Step S302, the determination image data before the abrasion that has been acquired is input to the learned NN 122 that has been read out, and the cause of occurrence of the coating irregularity is determined. Then the process goes to Step S104. When it is determined to be YES in Step S104, the process goes to Step S105, where it is determined that the probable cause of occurrence has been determined from the determination image data before the abrasion. Then the series of processing is ended.

When it is determined to be NO in Step S104, the process goes to Step S303. In Step S303, the determination unit 121a determines that determination image data, which is image data obtained by capturing an image of the surface in which at least a surface layer on the coating irregularity has been abraded, is required, and transfers this information to the output unit 124. The output unit 124 outputs this information to the output terminal 130.

Next, in Step S304, the acquisition unit 123 acquires the determination image data and transfers this data to the determination unit 121a. Next, in Step S305, the determination unit 121a inputs the determination image data before the abrasion that has been acquired to the learned NN 122, and determines the cause of occurrence of the coating irregularity. In Step S306, the determination unit 121a transfers the cause of occurrence that has been determined to the output unit 124, and the output unit 124 outputs this information to the output terminal 130. Then the series of processing is ended.

The probability of the result of the determination in Step S305 may be further checked and a correction determination image may be requested, as in Step S106 in FIG. 5. Further, in the second modified example as well, like in the first modified example, the learned NN may be prepared for each coating color, and the learned NN may be read out in accordance with the coating color that can be identified from the image data that has been acquired by the acquisition unit.

While the example in which the image data is used as the input information has been described in this embodiment including the modified examples, besides the image data, other information may be added to the training data and the data for determination. For example, temperature information, humidity information of the coating environment, and information on time when the coating is performed may be used as additional information for improving the accuracy of determination.

Further, as a matter of course, the causes of occurrence of the coating irregularity shown in FIG. 4 and the like are merely examples, and other causes of occurrence may be added to the determination target. Further, a plurality of pieces of learning image data are preferably prepared for one cause of occurrence. The coating irregularity is not limited to dust or air bubbles and may be generated by mixture of other paint, scattering of oil or the like.

Further, a camera fixing jig or the like for keeping the angle of view with respect to the coating surface constant may be used in such a way that the size of the coating irregularity becomes constant with respect to the image. In this case, the sizes of the coating irregularities of the same kind become substantially constant with respect to the image area, which contributes to improvement of the accuracy of determination of the cause of occurrence.

A (The) program can be stored and provided to a computer using any type of non-transitory computer readable media. Non-transitory computer readable media include any type of tangible storage media. Examples of non-transitory computer readable media include magnetic storage media (such as floppy disks, magnetic tapes, hard disc drives, etc.), optical magnetic storage media (e.g. magneto-optical disks), CD-ROM (compact disc read only memory), CD-R (compact disc recordable), CD-R/W (compact disc rewritable), and semiconductor memories (such as mask ROM, PROM (programmable ROM), EPROM (erasable PROM), flash ROM, RAM (random access memory), etc.). The program may be provided to a computer using any type of transitory computer readable media. Examples of transitory computer readable media include electric signals, optical signals, and electromagnetic waves. Transitory computer readable media can provide the program to a computer via a wired communication line (e.g. electric wires, and optical fibers) or a wireless communication line.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. An analysis apparatus configured to analyze a cause of occurrence of a coating irregularity, which is a coating defect that appears on a coating surface as a protrusion, the analysis apparatus comprising:
   a storage unit configured to store a learned neural network that has performed learning using a combination of learning image data obtained by capturing an image of a surface in which at least a surface layer of a coating layer stacked on the coating irregularity generated in the coating surface to be learned has been abraded and input data estimated by analyzing this coating irregularity as training data;
   an acquisition unit configured to acquire determination image data obtained by capturing an image of a surface in which at least a surface layer of a coating layer stacked on the coating irregularity generated in the coating surface to be determined has been abraded;
   a determination unit configured to input the determination image data acquired by the acquisition unit to the learned neural network read out from the storage unit and determine the cause of occurrence of the coating irregularity generated in the coating surface to be determined; and
   an output unit configured to output information regarding the cause of occurrence determined by the determination unit.

2. The analysis apparatus according to claim 1, wherein, when the coating irregularity occurs due to dust, each of the learning image data and the determination image data is image data obtained by capturing an image of the surface abraded in such a way that the dust is exposed.

3. The analysis apparatus according to claim 1, wherein, when the determination unit cannot make a determination that satisfies a predetermined determination criterion, the determination unit makes a determination that determination image data obtained by capturing an image of a surface in which the coating layer to be determined is further abraded is required.

4. The analysis apparatus according to claim 1, wherein
   the storage unit stores a plurality of learned neural networks for respective coating colors, and
   the determination unit selects the learned neural network that receives the determination image data based on a coating color indicated by the determination image data acquired by the acquisition unit.

5. The analysis apparatus according to claim 1, wherein
   the training data comprises learning image data before abrasion obtained by capturing an image of a surface before the coating layer is abraded,
   the acquisition unit acquires determination image data before the abrasion obtained by capturing an image of a surface in which the coating layer to be determined has not been abraded, and
   the determination unit inputs the determination image data before the abrasion acquired by the acquisition unit to the learned neural network read out from the storage unit, and determines the cause of occurrence of the coating irregularity generated in the coating surface to be determined.

6. The analysis apparatus according to claim 5, wherein the acquisition unit acquires the determination image data when the determination unit has not determined the cause of occurrence, and the determination unit inputs the determination image data acquired by the acquisition unit to the learned neural network and determines the cause of occurrence of the coating irregularity generated in the coating surface to be determined.

7. A non-transitory computer readable medium storing an analysis program configured to analyze a cause of occurrence of a coating irregularity, which is a coating defect that appears on a coating surface as a protrusion, the analysis program causing a computer to execute the following steps of:

an acquisition step for acquiring determination image data obtained by capturing an image of a surface in which at least a surface layer of a coating layer stacked on the coating irregularity generated in the coating surface to be determined has been abraded;

a reading step for reading out a learned neural network that has performed learning using a combination of learning image data obtained by capturing an image of a surface in which at least a surface layer of a coating layer stacked on the coating irregularity generated in the coating surface to be learned has been abraded and input data estimated by analyzing this coating irregularity as training data from a storage unit;

a determination step for inputting the determination image data acquired in the acquisition step to the learned neural network read out from the storage unit and determining the cause of occurrence of the coating irregularity generated in the coating surface to be determined; and an output step for outputting information regarding the cause of occurrence determined in the determination step.

* * * * *